United States Patent [19]

Allegretti et al.

[11] Patent Number: 5,002,206
[45] Date of Patent: Mar. 26, 1991

[54] DOUBLE TIP DRUG DISPENSING AND METERING DEVICE

[75] Inventors: John E. Allegretti, East Brunswick; Thomas E. Schlaudecker, Hamilton Square, both of N.J.

[73] Assignee: Merck & Co., Inc., Rahway, N.J.

[21] Appl. No.: 426,629

[22] Filed: Oct. 25, 1989

[51] Int. Cl.$^5$ .............................................. B65D 37/00
[52] U.S. Cl. ...................... 222/212; 222/331; 222/420; 222/482; 239/327; 239/390; 239/436
[58] Field of Search ............... 222/206, 211, 212, 478, 222/481, 209, 255, 482, 331, 420, 421; 239/442, 436, 390, 397, 327, 328

[56] References Cited

U.S. PATENT DOCUMENTS

| 2,874,881 | 2/1959 | Stull | 222/421 |
|---|---|---|---|
| 3,170,633 | 2/1965 | Castelli | 239/436 X |
| 3,340,873 | 9/1967 | Solowey | |
| 3,354,883 | 11/1967 | Southerland et al. | |
| 3,381,860 | 5/1968 | Amour | 239/327 X |
| 3,397,694 | 8/1968 | Ogle | |
| 3,411,503 | 11/1986 | Santomieri | |
| 3,464,414 | 9/1969 | Sponnoble | |
| 4,002,168 | 1/1977 | Petterson | 222/421 X |
| 4,030,664 | 6/1977 | Tisbo | 222/481 X |
| 4,330,531 | 5/1982 | Alliger | |
| 4,331,146 | 5/1982 | Brignoia | |
| 4,412,836 | 11/1983 | Brignoia | |
| 4,618,076 | 10/1986 | Silvenis | 222/331 |
| 4,809,914 | 3/1989 | Goncalves | 239/327 |
| 4,811,866 | 3/1989 | Golias | 222/420 X |
| 4,832,215 | 5/1989 | LeBlanc | 222/478 X |

FOREIGN PATENT DOCUMENTS 3223995 12/1983 Fed. Rep. of Germany ...... 239/304

Primary Examiner—Andres Kashnikow
Assistant Examiner—Gregory L. Huson
Attorney, Agent, or Firm—Manfred Polk; Joseph F. Diprima

[57] ABSTRACT

A double tip drug dispensing and metering device having a bellows or conventional squeeze body container between the double tips. The device being adapted to hold at least two substances in solution which are required to be separated until just prior to dispensation.

4 Claims, 5 Drawing Sheets

DOUBLE TIP DRUG DISPENSING AND METERING DEVICE

BACKGROUND OF THE INVENTION

Many drugs, particularly those used in treatment of various eye disorders, are administered in drop form. The drops of liquid are intended to free-fall onto the eye surface, where it is distributed across the exposed eye. Dosage of these ophthalmic drugs is often crucial. For example, lower than prescribed levels of the drugs can result in failure of treatment and consequent progression of the disease and higher levels can result in intractable side effects which can also interfere with successful resolution.

Complicating the administration of these drugs is the fact that they are often required several times a day and thus to be practical, must be administered by the patient rather than medical personnel who are formally trained in drug delivery. Patient administration of such drugs has resulted in two serious problems, namely, bottle contamination and flow rate which must be solved for medications to be successfully administered.

Container devices having multiple compartments for separately enclosed materials to be mixed prior to use are described in U.S. Pat. Nos. 3,340,873; 3,354,883; 3,397,694; 3,411,503; 4,331,146; 4,412,836; and 4,330,531, having a thin diaphrame-type membrane separating the two compartments. These systems are not considered entirely reliable due to its ability to maintain a fluid-tight seal between the compartments. U.S. Pat. No. 3,464,414 discloses a rigid walled two chambered mixing vial utilizing hydraulic pressure to dislodge a plug member between the two chambers.

SUMMARY OF THE INVENTION

This invention relates to a double tip drug dispensing/metering device adapted to hold at least two substances in solution which are required to be segregated until just prior to dispensation, and to provide a means for in vitro mixing and dispensing of the mixture. Accordingly, a mixture having a limited effective shelf-life once mixed may be preserved for a specific or indefinite period by maintaining separately the components with or without a preservative until use is desired. While one of the constituents must be liquid, the other component may be a liquid or a solid. However, the solid component must be in solution prior to entrance into the device.

Liquid dropper dispensers find use in many medicinal areas, particularly ophthalmic medication where contamination is a concern. Often dropper dispensers are of a plastic "squeeze" type whereby liquid is forced out by squeezing the dispenser and residual liquid and air are drawn into the dispenser when it is permitted to expand. Therefore, it is an object of this invention to provide a double tip dispensing/metering device wherein the upper tip serves as a dispensing/metering device and the lower tip serves as a means of diluent(s) transfer which is operable without the limitations presented in the prior art.

It is another object of this invention to provide a double tip dispensing/metering device that is operable by a patient in need of medication comprises of components which must be separated until use is required.

It is further object of this invention to provide a double tip dispensing/metering device adaptable to be used with a variety of dispensing means.

Additional objects of this invention will be apparent to persons of ordinary skill in the art upon reading the following detailed description and appended claims and upon reference of the accompanying drawings.

DETAILED DESCRIPTION OF THE INVENTION

It has been found that affixing a second (base) dropper tip to a single upper dropper tip dispensing/metering device permits two separate substances to be premixed at the desired time thereby increasing the individual shelf-life prior to mixing of each substance and reducing contamination when mixing is desired along with obtaining a metered delivery of the solution (wet/wet or wet/dry) through the upper dropper tip. The dispensing/metering device disclosed herein maintains the desired liquid(s) and/or solid drug substances in solution thereby enhancing the desired flow rate of said drug when passing through said upper tip of such device. As previously mentioned, patient administration of drugs has resulted in two serious problems, namely, (1) bottle contamination and (2) flow rate, which must be solved for these medications to be successfully administered. More detailed discussions of the problems are provided below:

(1) BOTTLE CONTAMINATION

Ideally, the pendent drop formed at the tip of conventional dropper bottle should be allowed to free-fall to the surface of the eye. In addition, the distance between the dropper tip and the surfaces of the eye should be kept reasonably close. This is important so that the momentum acquired by the free-falling drop will not be so great as to cause the drop to splatter on impact with the eye surface. These conditions: a free-falling pendent drop being discharged close to the eye surface, are readily accomplished by a trained professional. They are substantially more difficult when the drug is self-administered. Gauging such short distances is physiologically difficult due to the inability to focus, and in addition, the anticipation of impacting drop often causes a blink and subsequent loss of portions of the drop. As a result, the user may permit the dropper tip to inadvertantly contact the eye surface.

In either case, small amounts of eye liquids can thus be inadvertently permitted to comingle with the liquid of the drop to be delivered. When the pressure on the delivery bottle is relieved a small amount of the mixed liquids may be drawn back into the bottle. With time, the bacteria originally present in the eye, both normal and pathological, will be permitted access to a medium which may cause them to proliferate. Thus, subsequent drops of medication may re-introduce to the eye either excessive levels of typicallyy present bacteria, or large numbers of pathogens. Neither situation is acceptable.

To cope with the problem of contamination, drug manufacturers often introduce an antibacterial agent to the drug bottle. In most cases, this agent or preservative can only be very effective at supressing the growth of bacterial contaminants within the bottle for a specified period of time. Unfortunately, there exists a significant population of patients for whom these preservatives represent ocular irritants, or in more severe cases cause allergic reactions. Such untoward ocular reactions prohibit these patients from accessing the drug in this kind of packaging. For these patients, single-use, non-preserved drug packaging is a partial answer, but at a significantly increased cost and inconvenience.

(2) FLOW RATE

Dosage of ophthalmic drugs are regulated on the basis of drops applied to the eye. Formation of the drops is directly related to the flow rate of the liquid from the bottle. The drops fall from the dropper tip when the weight of the pendent drop exceeds the surface tension forces holding the drop to the dropper tip. In the ideal case, each drop should be identical to the previous one. However, in practice, other factors intervene to cause significant variation in drop size. One of the most significant is the rate of drop formation. If the drop is formed rapidly, more liquid can be "injected" into the body of to drop as it is beginning to break free. These drops will be larger, and thus will carry more drug, than if the bottle were squeezed very slowly. In extreme circumstances, the drug may be ejected in a steady stream.

The method and device of this invention overcomes three (2) serious problems, namely, it enhances uncontrolled flow rate and prolongs the shelf-life of at least two substances which are required to be separated prior to mixing and dispensing. Contamination of the liquid in the dropper bottle is overcome by several features incorporated into the dropper tip itself. In addition, these features act to restrict the rate of drop formation, irrespective of the variable pressure which may be brought to bear on the bottle walls by the user. Thus, with the flow rate metered, the drops possess a substantially more repeatale liquid volume.

A method for practicing the concepts of the invention disclosed herein is to hold at least two substances which are required to be separated until just prior to dispensation, and provide a means for in vitro mixing and dispensing of the mixture. The upper tip of the device disclosed herein functions as a dispensing/metering device and the lower tip functions as a transfer system for diluent(s) to enter into said device. The upper and lower tips are terminal components of a single device having an inner bellows or conventional squeeze body chamber having resillant walls containing the mixture for application.

BRIEF DESCRIPTION OF THE DRAWINGS

For a more complete understanding of the invention, reference should be made to the embodiment illustrated in greater detail in the accompanying drawings and described below by way of example of the invention.

In the drawings:

Figure 1:
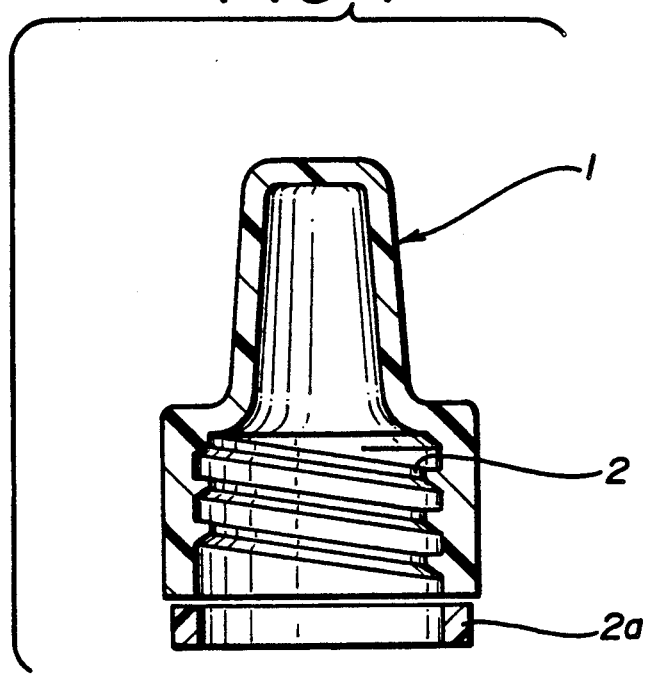
Figure 2:
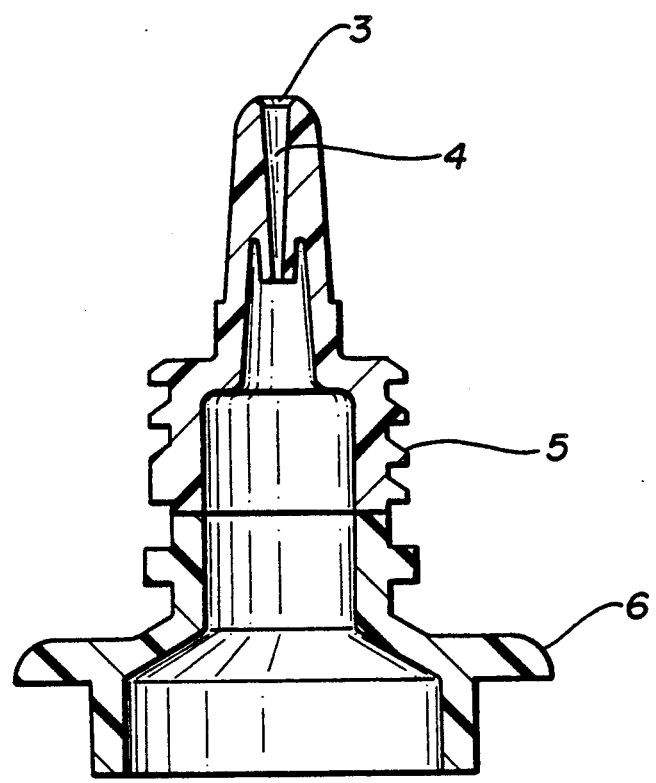

FIG. I shows a cross-sectional view of the upper dropper cap with tamper-evident (T/E) collar that screws onto said upper dropper tip.

FIG. II shows a cross-sectional view of the upper dispensing/metering dropper tip to be permanently affixed to a common bellows or conventional squeeze chamber.

FIG. III shows a cross-sectional view of a bellows or conventional squeeze chamber having permanently affixed a lower dropper transfer tip with reverse threaded means for attachment of the base cap.

FIG. IV shows a cross-sectional view of the device disclosed herein having permanently affixed the upper and lower dropper tips having a common bellows or conventional squeeze chamber.

FIG. V shows a cross-sectional view of a the base reverse thread screw cap which covers the lower transfer tip and serves as a base for the dispensing/metering device. It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be further understood, of course, that the invention is not necessarily limited to the particular embodiments illustrated herein.

In general, the dispensing/metering device described herein consists of an upper T/E cap (1) having screw on threaded attachment (2) and T/E collar (2a) for covering upper tip (3) as shown in FIG. II. The upper cap is used primarily as a protective cover for the upper tip of the device. FIG. II consists of a metered dropper tip having orifice (3) being connected to dropper chamber (4) and connecting screw threads (5) for allowing the upper cap described in FIG. I to attached and cover said upper tip of FIG. II. Upper tip (FIG. II) is permanently connected (preferably by sonic welding or the use of an adhesive system) to lower attachment arm (6) of FIG. II and the upper bellow (8) of FIG. III thereby connecting both upper and lower dropper tips as shown in FIG. IV. Said lower (base) dropper tip have conventional squeeze or bellow walls (9) reverse thread screw (10) for attachment of base cap (FIG. V), transfer tip channel (11) for entrance of medicinal(s) into storage bellow chamber (9) through sealed tip orifice (12) being located at the base of lower dropper orifice tip (12) which connects with passage channel (11).

Figure 3:
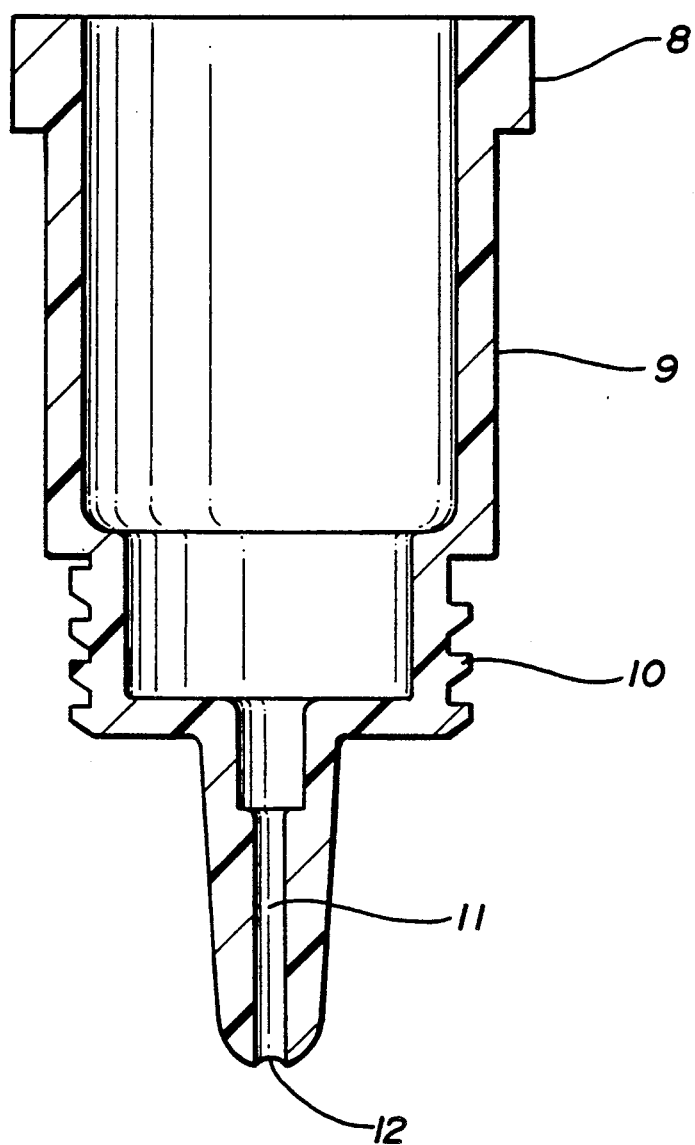
Figure 4:
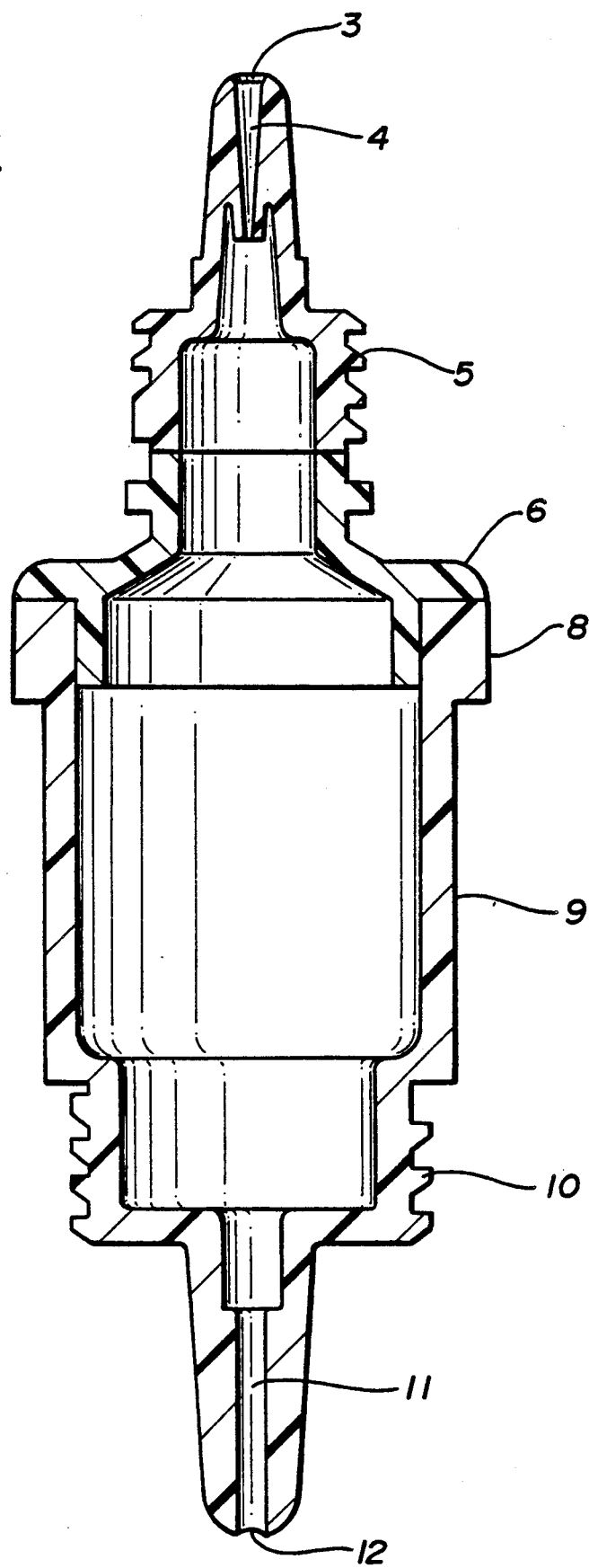
Figure 5:
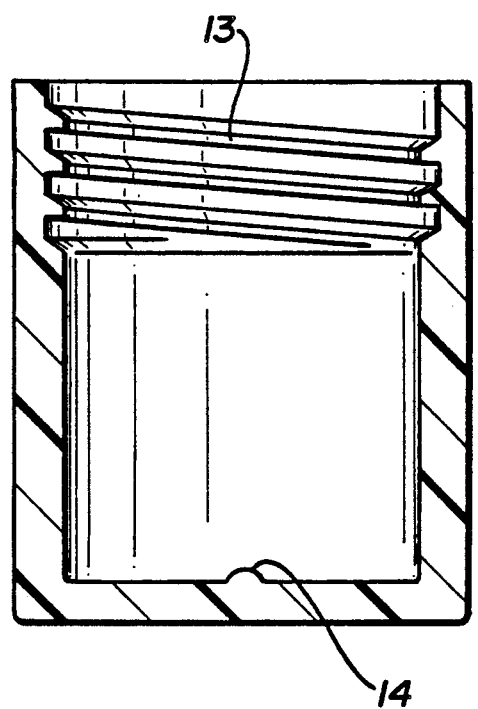

In FIG. 3, the base dropper transfer tip (12) of the device disclosed herein is covered by a reverse thread screw cap FIG. V having reverse threads screw (13) and tip seal (14) for permanently sealing the lower tip after transfer of the medicinal(s) (wet/wet or wet/dry) into storage chamber (9).

The dispensing/metering device disclosed herein is useful in administering at least two substances which are required to be separated until just prior to dispensation. Said device consists of two dropper tips, the upper tip serving as a dispensing/metering device tip and the lower tip serving as a transfer device for substance(s) required to be segregated until time for pre-mixing.

In practicing the concept of this invention, at least two diluents (wet/wet or wet/dry) are separately pre-mixed with or without a preservative until complete solution is obtained. The diluents are then transferred into the bellow or conventional squeeze body container (6 and 9) via lower base transfer orifice tip (12) of the device. If one of said diluent(s) is a solid, then complete solution is required before transferring through said base transfer tip. It is not critical as to which diluent is first transferred into the bellows or conventional squeeze body container (6 and 9). In fact, the diluents can be pre-mixed and then transferred into the body container of the device and stored until treatment is desired.

In FIG. II, the orifice progressively gets larger from its inception to point (3). The lower part of the orifice (3) has a dimension of from 0.002 to 0.010 ±0.001 inch, preferably from 0.004 to 0.008 ±0.001 inch and most preferably 0.006 ±0.001 inch. The upper part of orifice (3) at point (3) has a demension of 0.060 to 0.10 ±0.005 inch, preferable 0.075 to 0.25 ±0.005 inch and most preferable 0.093 ±0.005 inch.

In FIG. III, one skilled in the art can readily appreciate that the dimensions of transfer tip channel (11) which connects to orifice (12) is not critical. In practicing the concept of this invention, it is found that dimensions in the range of 0.015 to 0.040 ±0.005 inch are applicable with 0.023 ±0.005 inch being preferred.

What is claimed:

1. A double tip dispensing and metering device comprising:
   (a) an upper metering tip for dispensing fluid in drop like form from said device and a lower transfer tip for receiving a product into said device, both coaxially located at opposite ends of said device and being separated by a resillantly deformable wall chamber for selectively placing the contents of said chamber under a dispensing pressure or receiving vacuum,
   (b) a plugging means for selectively sealing said lower transfer tip, and
   (c) a means in said upper tip for dispensing a predetermined volume of substance from said device.

2. The device of claim 1, wherein said upper metering tip means is an orifice channel with a diameter ranging lower to upper progressively from 0.002 to 0.010 ±0.005 inch to b 0.075 to 0.25 ±0.005 inch.

3. The device of claim 2, wherein said lower range is from 0.004 to 0.008 ±0.001 inch and said upper range is from 0.060 to 0.10 ±0.005 inch.

4. The device of claim 3, wherein said lower range is 0.006 ±0.001 inch and said upper range is 0.093 ±0.005 inch.

* * * * *